United States Patent [19] [11] 4,333,943
Kurchacova et al. [45] Jun. 8, 1982

[54] ETHYL 3-(3-INDOLYL)-3-(5-TETRAZOLYL) PROPIONATE COMPOUNDS USED AS ANTI-HYPERTENSIVE AGENTS

[75] Inventors: Elva Kurchacova; Max E. Safdy, both of Elkhart, Ind.

[73] Assignee: Miles Laboratories, Inc., Elkhart, Ind.

[21] Appl. No.: 216,516

[22] Filed: Dec. 15, 1980

Related U.S. Application Data

[63] Continuation of Ser. No. 143,319, Apr. 24, 1980, abandoned.

[51] Int. Cl.³ .................... A61K 31/41; C07D 257/04
[52] U.S. Cl. .................................... 424/269; 548/253
[58] Field of Search ..................... 548/253; 424/269

[56] References Cited

U.S. PATENT DOCUMENTS 3,705,894 12/1972 Gerzon et al. ..................... 424/269

OTHER PUBLICATIONS

Snyder et al., J. Am. Chem. Soc., 66, 200–204 (1944).

Primary Examiner—Anton H. Sutto
Assistant Examiner—D. B. Springer
Attorney, Agent, or Firm—Jerome L. Jeffers

[57] ABSTRACT

Disclosed are novel ethyl 3-(3-indolyl)-3-(5-tetrazolyl) propionate compounds characterized by the formula:

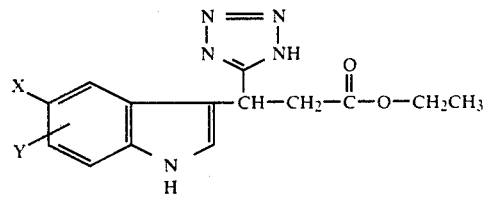

wherein X is H or methoxy and Y is H, Cl or methoxy. These compounds are useful as antihypertensive agents.

6 Claims, No Drawings

ETHYL 3-(3-INDOLYL)-3-(5-TETRAZOLYL) PROPIONATE COMPOUNDS USED AS ANTI-HYPERTENSIVE AGENTS

This is a continuation of application Ser. No. 143,319, filed Apr. 24, 1980, now abandoned.

BACKGROUND OF THE INVENTION

P. F. Juby et al. disclose in *J. Med. Chem.*, 12, 396–341(1969), 3-(5-tetrazolyl) indoles of the formula:

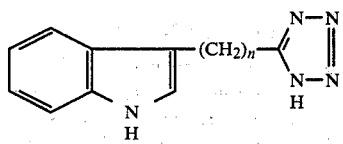

where n is 0 or 2. These compounds, which are prepared from the corresponding nitriles, are useful as anti-inflamatory agents.

Compounds of the formula

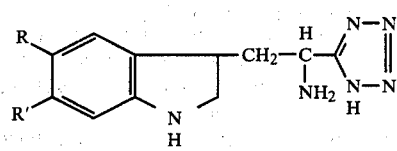

where R and R' are hydrogen, halo, lower alkyl or loweralkoxy are disclosed in U.S. Pat. No. 3,615,700 issued Oct. 26, 1971. These compounds are taught to be useful as nonnutritive sweetening agents.

SUMMARY OF THE INVENTION

The present invention involves novel ethyl 3-(3-indolyl)-3-(5-tetrazolyl) propionate compounds of the formula:

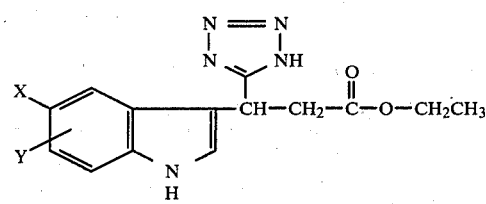

wherein X is H or methoxy and Y is H, Cl or methoxy.

DESCRIPTION OF THE INVENTION

The ethyl 3-(3-indolyl)-3-(5-tetrazolyl) propionates of the present invention II are prepared by refluxing, in an appropriate solvent such as dimethylformamide (DMF), the corresponding 3-nitrile precursor I, prepared as described by Perron et al. in J.O.C. 24 1165 (1959), with sodium azide and ammonium chloride.

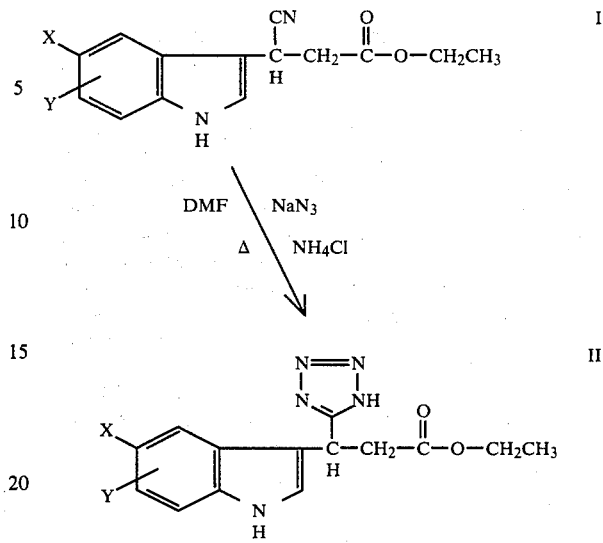

The preparation of these compounds is further illustrated by the following examples:

EXAMPLE I

Ethyl 3-(Indolyl)-3-(5-Tetrazolyl) Propionate(TR-3383)

Ethyl 3-cyano-3-(3-indolyl) propionate, Compound I where X and Y are H, (5 g, 0.022 mole) was dissolved in 30 ml of dry DMF. Ammonium chloride (1.75 g, 0.033 mole) and sodium azide (2 g, 0.033 mole) was added and the mixture refluxed at 120° C. for 24 hours at which point the mixture was evaporated to dryness in vacuo. The solid mixture was partitioned with 25 ml of water, 7 ml of concentrated HCl and ethyl acetate. The organic phase was washed three times with brine, dried over MgSO$_4$, filtered, concentrated in vacuo until solid material was seen and cooled. The solid was then removed by filtration and dried. Yield 3.1 g (55% theory), M.P. 178°–179° C.

Anal. Calcd for C$_{14}$H$_{15}$N$_5$O$_2$: C, 58.99; H, 5.31; N, 24.58 Found: C, 57.61; H, 5.26; N, 24.61

EXAMPLE II

Ethyl 3-[3-(5-Methoxyindolyl)]-3-(5-Tetrazolyl) Propionate (TR-3384)

Ethyl 3-cyano-3-[3-(methoxyindolyl]propionate, Compound I where X=OCH$_3$ and Y=H (4 g, 0.15 mole) was dissolved in 20 ml of dry DMF. Ammonium chloride (1.75 g, 0.033 mole) and sodium azide (2.1 g, 0.033 mole) was added and the mixture was refluxed at 120° C. for 24 hours whereupon the reaction mixture was evaporated to dryness. The solid residue was partitioned with 30 ml of water, 8 ml of conc. HCl and ethyl acetate. The organic phase was separated, washed three times with brine, dried over MgSO$_4$, filtered and concentrated in vacuo.

The residue crystallized when triturated with ethyl acetate and Skelly B (a mixture of saturated hydrocarbons of from C$_5$–C$_7$) to yield 2 g (42% theory), M.P. 122°–124° C.

Anal. Calcd. for C$_{15}$H$_{17}$N$_5$O$_3$: C, 57.20; H, 5.44; N, 22.24. Found: C, 56.43; H, 5.53; N, 22.40.

EXAMPLE III

Ethyl 3-[3-(4-Chloroindolyl)]-3-(5-Tetrazolyl) Propionate (TR-3385)

Ethyl 3-cyano-3-[4-chloroindolyl]propionate, Compound I where X=H and Y=Cl (5 g, 0.018 mole) was dissolved in 30 ml of dry DMF. Ammonium chloride (1.75 g, 0.033 mole) and sodium azide (2.1 g, 0.033 mole) were added and the mixture refluxed at 120° C. for 24 hours. The mixture was evaporated to dryness in vacuo. The solid mixture was partitioned with 30 ml of water, 10 ml of concentrated HCl and ethyl acetate. The organic phase was separated, washed three times with brine, dried over MgSO4, filtered and concentrated in vacuo.

The residue crystallized when triturated with ethyl acetate and Skelly B to yield 4.8 g (82% theory), M.P. 204°–205° C.

Anal. Calcd. for $C_{14}H_{14}ClN_5O_2$: C, 52.61; H, 4.42; N, 21.92. Found: C, 52.84; H, 4.48; N, 22.78.

EXAMPLE IV

Ethyl 3-[3-(6-Chloroindolyl)]-3-(5-Tetrazolyl) Propionate (TR-3386).

Ethyl 3-cyano-3-[6-chloroindolyl]propionate, Compound I where X=H and Y=Cl, (5 g, 0.018 mole) was dissolved in 30 ml of dry DMF. Ammonium chloride (1.75 g 0.033 mole) and sodium azide (2.1 g, 0.033 mole) was added and the mixture refluxed at 120° C. for 24 hours. The mixture was evaporated to dryness in vacuo. The solid mixture was partitioned with 30 ml of water, 10 ml of concentrated HCl and ethyl acetate. The organic phase was separated, washed three times with brine, dried over MgSO4, filtered and concentrated in vacuo.

The residue crystallized when triturated with ethyl acetate and Skelly B to yield 2.0 g (36% theory), M.P. 186°–187° C. 186°–187° C.

Anal. Calcd for $C_{14}H_{14}ClN_5O_2$: C, 52.61; H, 4.42; N, 21.92. Found: C, 52.70; H, 4.19; N, 22.65.

EXAMPLE V

Ethyl 3-[3-(5,6-Dimethoxyindolyl)]-3-(5-Tetrazoyl) Propionate (TR-3407)

Ethyl 3-cyano-3-[5,6-methoxyindolyl]propionate, Compound I where X=OCH3 and Y=OCH3, (6 g, 0.021 mole) was dissolved in 30 ml of dry DMF. Ammonium chloride (1.75 g, 0.033 mole) and sodium azide (2.1 g, 0.033 mole) was added and the mixture refluxed at 120° C. for 24 hours at which point the mixture was evaporated to dryness in vacuo. The solid mixture was partitioned with 30 ml of water, 10 ml of concentrated NCl and ethyl acetate. The organic phase was separated washed three times with brine, dried over MgSO4, filtered and concentrated in vacuo.

The residue crystallized when triturated with ethyl acetate and Skelly B to yield 4 g (55% theory) M.P. 174°–175° C.

Anal. Calcd for $C_{16}H_{19}N_5O$: C, 55.63; H, 5.54; N, 20.28. Found: C, 54.81; H, 5.68; N, 20.18.

EXAMPLE VI

The compounds prepared as described above were tested for anti-hypertensive activity in rats and cats using the following procedures:

EXPERIMENTS IN RATS

The acute antihypertensive activity of test compounds was determined in rats made hypertensive by the procedure of A. Grollman, Proc. Soc. Exper. Biol. Med. 57:102 (1944) by applying a figure of eight ligature to one kidney and removing the contralateral kidney two weeks later. At least four weeks after the second operation, the rats were subjected to indirect systolic blood pressure measurements with an occluding cuff and pulse sensor applied to the tail. Measurements were made before and at 1, 2, 4, 6 and 8 hours after the oral administration of the test compounds at a dose of 10 mg/kg. Each compound was tested initially in five rats and if it elicited a significant decrease in pressure at any of the observation periods, it was tested in another five animals and results of the two experiments were averaged. Statistical significance of differences between initial and post treatment values was determined by Wilcoxon's signed rank test (F. Wilcoxon and R. A. Wilcox, Some Rapid Approximate Statistical Procedures, Lederle Laboratories, Pearl River, 1964).

EXPERIMENTS IN CATS

The acute effects of test compounds on blood pressure were determined in cats anesthetized with chloralose. Cannulas were inserted in a femoral artery for blood pressure recording and in a sephenous vein for drug administration. After a period of 10 minutes of stable recordings of blood pressure, the test compound was administered intravenously at 10 mg/kg. Each compound was evaluated in one animal. Changes in mean blood pressure were determined by averaging values observed at 10, 20, 30, 40, 50 and 60 minutes after injection.

The results of these tests are summarized in Table I:

TABLE I

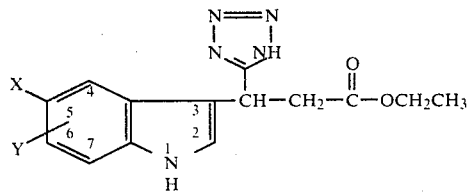

| COMPOUND | X | Y | Rat blood Pressure, mm Hg | | | | | | | Cat BP, mm Hg | |
|---|---|---|---|---|---|---|---|---|---|---|---|
| | | | $N^1$ | $C^2$ | 1hr | 2hr | 4hr | 6hr | 8hr | $C^2$ | Δ |
| TR-3383 | H | H | 10 | 192 | −4 | −22* | −27* | −22* | −7 | 168 | −3 |
| TR-3384 | −OCH3 | H | 10 | 195 | −16 | −21 | −25* | −16 | −11 | 136 | −14 |
| TR-3385 | H | 4-Cl | 5 | 194 | −4 | −12 | −5 | −2 | +4 | 135 | −32 |
| TR-3386 | H | 6-Cl | 5 | 202 | −5 | +2 | −4 | −17 | −11 | 175 | −26 |

TABLE I-continued

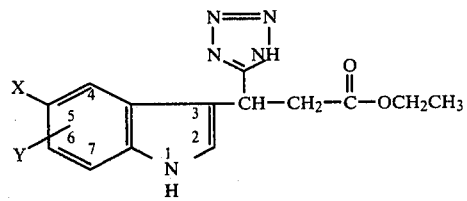

| COMPOUND | X | Y | Rat blood Pressure, mm Hg | | | | | | Cat BP, mm Hg | |
|---|---|---|---|---|---|---|---|---|---|---|
| | | | $N^1$ | $C^2$ | 1hr | 2hr | 4hr | 6hr | 8hr | $C^2$ | Δ |
| TR-3407 | —OCH₃ | 6-OCH₃ | 10 | 199 | −11 | −15 | −20 | −25 | −14 | 164 | −6 |

[1] N = number of test animals
[2] C = initial value
*statistically significant

The compounds of this invention possess unexpected pharmacological properties that render them useful as therapeutic agents for the treatment of hypertension in an individual for whom such therapy is indicated. The term individual is intended to mean a human being or an experimental animal that is used as a model for a human being. The effective dosage may vary from individual to individual but is easily determined by one skilled in the art without undue experimentation. Dose forms for the administration of the compounds of this invention may be prepared by recognized methods in the pharmaceutical sciences. Particular dose forms can be administered by conventional known methods of therapeutic administration such as oral, intravenous, parenteral or the like.

What is claimed is:

1. A method for treating hypertension in an individual for whom such therapy is indicated which method comprises administering to the individual a therapeutically effective amount of an ethyl 3-(3-Indolyl)-3-(5-tetrazolyl) propionate of the formula:

wherein X is H or methoxy and Y is H, Cl or methoxy.

2. The method of claim 1 wherein the compound administered is further defined in that X and Y are H.

3. The method of claim 1 wherein the compound administered is further defined in that X is —OCH₃ and Y is H.

4. The method of claim 1 wherein the compound administered is further defined in that X is —OCH₃ and Y is 6-OCH₃.

5. The method of claim 1 wherein the compound administered is further defined in that X is H and Y is 6-Cl.

6. The method of claim 1 wherein the compound administered is further defined in that X is H and Y is 6-OCH₃.

* * * * *